United States Patent [19]

Rajakhyaksha

[11] Patent Number: 4,837,026
[45] Date of Patent: Jun. 6, 1989

[54] TRANSDERMAL AND SYSTEMIC PREPARATION AND METHOD

[76] Inventor: Vithal J. Rajakhyaksha, 27436 Esquina, Mission Viejo, Calif. 92691

[21] Appl. No.: 783,621

[22] Filed: Oct. 3, 1985

[51] Int. Cl.$^4$ ............................................. A61F 13/00
[52] U.S. Cl. .................................. 424/449; 424/448; 424/447; 514/169; 514/788
[58] Field of Search ............... 424/449; 514/946, 169, 514/947, 788, 24, 89, 315

[56] References Cited

U.S. PATENT DOCUMENTS

| | | | |
|---|---|---|---|
| 3,960,922 | 6/1976 | Baket et al. | 540/607 |
| 3,966,806 | 6/1976 | Baker et al. | 540/607 |
| 3,989,815 | 11/1976 | Rajakhyaksha | 514/24 |
| 3,989,816 | 11/1976 | Rajakhyaksha | 514/24 |
| 3,991,203 | 11/1976 | Rajakhyaksha | 514/24 |
| 4,007,268 | 2/1977 | Voorhees | 514/81 |
| 4,021,224 | 5/1977 | Pallos et al. | 546/245 |
| 4,118,500 | 10/1978 | Mitzlaff et al. | 514/210 |
| 4,122,170 | 10/1978 | Rajakhyaksha | 514/24 |
| 4,264,594 | 4/1981 | McGovern et al. | 260/239 B |
| 4,312,872 | 1/1982 | Junge et al. | 514/315 |
| 4,316,893 | 2/1982 | Rajakhyaksha | 514/24 |
| 4,415,563 | 11/1983 | Rajakhyaksha | 514/24 |
| 4,423,040 | 12/1983 | Rajakhyaksha | 514/24 |
| 4,424,210 | 1/1984 | Rajakhyaksha | 514/24 |
| 4,444,762 | 4/1984 | Rajakhyaksha | 514/24 |
| 4,621,143 | 11/1986 | McGovern et al. | 546/245 |
| 4,743,588 | 5/1988 | Nurejovsky et al. | 514/29 |

FOREIGN PATENT DOCUMENTS

| | | |
|---|---|---|
| 29617 | 6/1981 | European Pat. Off. . |
| 164998 | 12/1985 | European Pat. Off. . |
| 45-22121 | 7/1970 | Japan . |
| 56-020572 | 2/1981 | Japan ................................. 540/607 |

*Primary Examiner*—Thurman K. Page
*Assistant Examiner*—Len P. Horne
*Attorney, Agent, or Firm*—Grant L. Hubbard

[57] ABSTRACT

A composition useful for topically administering physiologically active agents through the skin and mucous membranes of humans and animals in a transdermal device or formulation for systemic use or to the skin of humans and animals for localized use comprising an effective amount of a physiologically active agent and a non-toxic, effective penetrating amount of a compound having the structural formula

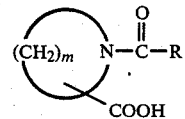

where R is an alkyl group with 1 to 19 carbon atoms, and m is 4, 5 or 6 is disclosed.

3 Claims, No Drawings

TRANSDERMAL AND SYSTEMIC PREPARATION AND METHOD

BACKGROUND OF THE INVENTION

Many physiologically active agents are best applied topically to obtain desirable results. Topical application, in the form of creams, lotions, gel, solution, et., largely avoids side effects of the agents and permits high level concentrations of the agents.

Some therapeutive drugs may also be administered for systemic use through the skin or other body membranes including intranasal and intravaginal application of humans and other animals, utilizing a transdermal device or formulated in a suppository or aerosol spray. For some years, pharmaceutical researchers have sought an affective means of introducing drugs into the bloodstream by applying them to the unbroken skin. Among other advantages, such administration can provide a comfortable, convenient and safe way of giving many drugs now taken orally or infused into veins or injected intramuscularly.

Using skin as the portal for drug entry offers unique potential, because of transdermal delivery permits close control over drug absorption. For example, it avoids factors that can cause unpredictable absorption from gastrointestinal tract, including: changes in acidity, motility, and food content. It also avoids initial metabolism of the drug by the liver, known as the first pass effect. Thus, controlled drug entry through skin can achieve a high degree of control over blood concentrations of drug.

Close control over drug concentration in blood can translate readily into safer and more comfortable treatment. When a drug's adverse effects occur at higher concentrations than its beneficial ones, rate control can maintain the concentration that evoke only—or principally the drug's desired actions. This ability to lessen undesired drug actions can greatly reduce the toxicity hazards that now restrict or prevent the use of many valuable agents. many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal systems that require application infrequently—in some cases, only once or twice weekly—and reduce adverse effects.

Transdermal delivery is feasible for drugs effective in amounts that can pass though the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, those susceptible to a higher first pass liver metabolism or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone difficiency, respiratory ailments, and pain relief.

Percutaneous administration can have the advantage of permitting continuous administration of drug to the circulation over prolonged period of time to obtain a uniform delivery rate and blood level of drug. Commencement and termination of drug therapy are initiated by the application and removal of the dosing devices from the skin. Uncertainties of administration through the gastrointestinal tract and the inconvenience of administration by injection are eliminated. Since a high concentration of drug never enters the body, problems of pulse entry are overcome and metabolic half-life is not a factor of controlling importance.

The greatest problems in applying physiologically active agents topically or transdermally is that the skin is an effective barrier to penetration. The epidermis of the skin has an exterior layer of dead cells called the stratum corneum which is tightly compacted and oily and which provides an effective barrier against gaseous, solid or liquid chemical agents, whether used alone or in water or in oil solutions. If a physiologically active agent penetrates the stratus corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use of treating such conditions as inflammation, acne, psoriasis, herpes simplex, eczema, infections caused by fungi, viruses and other microorganisms, or other disorders or conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellants and the like.

Physiologically active agents may be applied to the locally affected parts of the body in the form of a solution, cream, lotion or gel utilizing the vehicle system described herein. These agents may also be delivered for systemic use utilizing the vehicle system in a transdermal patch. Vehicles such as USP cold cream, ethanol and various ointments, oils, solvents and emulsions have been used heretofore to apply physiologically active ingredients locally. Most such vehicles are not effective to carry significant amounts of physiologically active agents into and through the skin. One such vehicle is dimethyl sulfoxide, which is described in U.S. Pat. No. 3,551,554.

My previous inventions disclosed in U.S. Pat. Nos. 3,989,816; 3,991,203; 4,122,170; 4,316,893; 4,415,563; 4,423,040; 4,424,210; 4,444,762 describe a method for enhancing the topical administration of physiologically active agents by combining such an agent with an effective amount of a penetration enhancer and applying the combination topically to humans or animals, in the form of solution, cream, gels, lotions etc. This prior art discloses N-alkyl substituted cyclic lactams as penetration enhancers.

My related U.S. Pat. No. 4,405,616, describes a method for administering systemically active agents through the skin or other body membranes of humans and animals, utilizing a transdermal device or formulation containing an effective amount of a suitable membrane penetration enhancer selected from the disclosed N-alkyl substituted cyclic lactams.

Penetration enhancers for enhancing systemic administration of therapeutic agents transdermally disclosed in the art include dodecyl pyrrolidone, dimethyl lauramide and dimethyl sulfoxide. The prior art states that these agents may be used prior to or concurrently with administration of the active agent, e.g. see U.S. Pat. Nos. 4,031,894; 3,996,934 and 3,921,636.

SUMMARY OF THE INVENTION

The invention relates to compositions for carrying physiologically active agents through body membranes such as skin and for retaining these agents in body tissues and further relates to a method of administering systemically active agents through the skin or other body membranes of humans and animals, utilizing a transdermal device or formulation, containing an effective, non-toxic amount of a membrane penetration enhancer having the structural formula I:

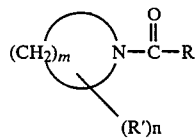

(I)

where,
R is an alkyl group with from 1 to 19 carbon atoms;
wherein
m=4, 5 and 6
n=0–4
and
R′=H or COOH
In one preferred embodiment, R is 6 to 19
In another preferred embodiment of

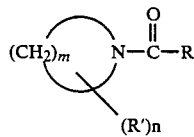

where m is 4 to 6, R is 1–19, R′ is H and n is 1.
The preferred compound is 1-dodecanoylhexahydro-1H-azepine.
In another preferred embodiment,

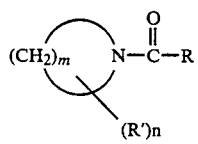

m is 4 to 6, R is 1 to 19, R′ is COOH and n is 1. The preferred compounds are in which m is 4 and 5, R′ is 2-COOH, and R is 11, for example,
1-dodecanoyl-2-carboxypyrrolidine
and
1-dodecanoyl-2-carboxypiperidine.

It has been found that the physiologically active agents are carried through body membranes by the claimed penetration enhancers and are retained in the body tissue when applied topically in form of a cream, gel or lotion or absorbed systemically when applied in the form of a transdermal device or formulation, for example, as a rectal or vaginal suppository, as a nasal spray or when incorporated in a vaginal sponge.

DETAILED DESCRIPTION OF THE INVENTION

Typical examples of compounds included in the foregoing formula I of this invention are the following:
(1) 1-butyrylpyrrolidine
(2) 1-pentanoylpyrrolidine
(3) 1-hexanoylpyrrolidine
(4) 1-octanoylpyrrolidine
(5) 1-nonanoylpyrrolidine
(6) 1-decanoylpyrrolidine
(7) 1-dodecanoylpyrrolidine
(8) 1-tetradecanoylpyrrolidine
(9) 1-hexadecanoylpyrrolidine
(10) 1-pentanoylpiperidine
(11) 1-hexanoylpiperidine
(12) 1-heptanoylpiperidine
(13) 1-octanoylpiperidine
(14) 1-nonanoylpiperidine
(15) 1-decanoylpiperidine
(16) 1-dodecanoylpiperidine
(17) 1-tetradecanoylpiperidine
(18) 1-hexadecanoylpiperidine
(19) 1-butyrylhexahydro-1H-azepine
(20) 1-pentanoylhexahydro-1H-azepine
(21) 1-hexanoylhexahydro-1H-azepine
(22) 1-heptanoylhexahydro-1H-azepine
(23) 1-octanoylhexahydro-1H-azepine
(24) 1-nonanoylhexahydro-1H-azepine
(25) 1-decanoylhexahydro-1H-azepine
(26) 1-dodecanoylhexahydro-1H-azepine
(27) 1-tetradecanoylhexahydro-1H-azepine
(28) 1-hexadecanoylhexahydro-1H-azepine
(29) 1-butyryl-2-carboxypyrrolidine
(30) 1-hexanoyl-2-carboxypyrrolidine
(31) 1-octanoyl-2-carboxypyrrolidine
(32) 1-decanoyl-2-carboxypyrrolidine
(33) 1-dodecanoyl-2-carboxypyrrolidine
(34) 1-tetradecanoyl-2-carboxypyrrolidine
(35) 1-hexadecanoyl-2-carboxypyrrolidine
(36) 1-hexanoyl-2-carboxypiperidine
(37) 1-octanoyl-2-carboxypiperidine
(38) 1-decanoyl-2-carboxypiperidine
(39) 1-dodecanoyl-2-carboxypiperidine
(40) 1-tetradecanoyl-2-carboxypiperidine
(41) 1-hexadecanoyl-2-carboxypiperidine
(42) 1-hexanoyl-3-carboxypiperidine
(43) 1-octanoyl-3-carboxypiperidine
(44) 1-decanoyl-3-carboxypiperidine
(45) 1-dodecanoyl-3-carboxypiperidine
(46) 1-tetradecanoyl-3-carboxypiperidine
(47) 1-hexadecanoyl-3-carboxypiperidine
(48) 1-hexanoyl-4-carboxypiperidine
(49) 1-octanoyl-4-carboxypiperidine
(50) 1-decanoyl-4-carboxypiperidine
(51) 1-dodecanoyl-4-carboxypiperidine
(52) 1-tetradecanoyl-4-carboxypiperidine
(53) 1-hexadecanoyl-4-carboxypiperidine The following compounds, encompassed by general formula I of this invention are known in the literature.

Compounds, 14 and 23-25 were evaluated for pungency [Rice et. a., J. Amer. Chem. Soc. 76,3730 (1954)]. Compounds 2-28 were evaluated for insect repellent activity [McGovern et. al., J. Ga. Entomol. Soc. 14,166 (1979); Alexander et al., J. Econ. Entomol., 56, 58 (1963); J. Chem. Eng. Data, 7,263 (1962); Davydova et al., Chem. Abstr., vol. 71, 122670j (1969); compounds 15 and 25 for antimicrobial activity [Novak et al., J. Amer. Oil Chem. Soc. 46,249 (1969); compounds 10-12 and 18 mimicking pepper constituents [Staudinger et. al., Ber., 56B, 699 (1923)]; compounds 29-32, 34 and 35, are known [Kikuchi et. al., Biochim. Biophys. Acta, 744,180 (1983)] as the substrates for the enzyme Proline Acylase. Compound 33 is known in the literature to possess plant growth regulating activity [Kider et. al., Agric. Biol. Chem., 40,1551, (1976)]; and compound 33 as a surface active agents for thermal denaturation of DNA [Tsuji, J. Amer. Oil Chem. So., 54,585 (1977)]. Compounds 44-53 to my knowledge are novel. The use of the compounds of the present invention as penetration enhancers is, however, novel and not predictable from the prior art.

The compounds covered by the general formula I may be prepared by any of the processes known for the preparation of acid amides. For example, (1) a carboxylic acid, R—COOH, is made to react directly with an amine of the formula II,

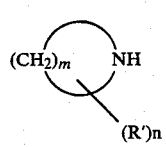

(II)

(wherein m, n, R and R' are as defined above) in the absence or presence of such dehydrating agents as a disubstituted carbodiimide compound, carbonyl diimidazole, p-toluenesulphonic acid, p-toluenesulphonyl chloride or acetic anhydride [Starkov et. al., Chem. Abstr., 72,31583 (1970)], in an aqueous or organic solvent, (2) a carboxylic acid halide, R—CO—X (where X is Cl or Br), prepared from a carboxylic acid, R—COOH, and the resulting acid halide is treated with at least an equimolar amount of the amine II, in the presence of a basic condensing agent [Alexander et. al., J. Econ. Entomol., 56,58 (1963); Kukuchi et. al., Biochim. Biophys. Acta 744,180 (1963)], (3) a lower alkyl ester of a carboxylic acid, R—COOR$_1$ (where R$_1$ is lower alkyl group with 1-3 carbons) is made to react directly with the amine, II, in the presence or absence of a solvent and condensing agent, (4) a mixed acid anhydride of a carboxylic acid of the formula,

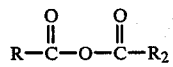

(wherein R is as defined above and R$_2$ is an alkyl or haloalkyl radical having 1-20 carbon atoms) is made to react with the amine, II, in the presence of a basic condensing catalyst, (5) amine of formula II is treated with a carboxylic acid in the presence of trimethylaminoborane in an aromatic hydrocarbon solvent, such as xylene [Trapani et. al., Synthesis, 1013 (1983)] or (6) transamidation of formylpiperidine and formylhexamethyleneimine with a carboxylic acid over 220 C [Naumov et. al., Chem. Abstr., 76, 85678u (1972)].

The compounds of the present invention may be used as penetration enhancers in the same manner as described in my U.S. Pat. Nos. 3,989,816; 3,991,203; 4,415,563; 4,122,170; 4,316,893; 4,423,040 4,424,210 and 4,444,762, which are hereby incorporated by reference.

The compounds of the present inventions are useful as penetration enhancers for a wide range of physiologically active agents and the compositions disclosed herein are useful for topical and transdermal therapeutic effect of these agents. Typically systemically active agents which may be delivered transdermally are therapeautic agents which are sufficiently potent such that they can be delivered through the skin or other membranes to the bloodstream in sufficient quantities to produce the desired therapeutic effect. In general this includes agents in all of the major therapeutic areas including, but not limited to, anti-infectives, such as antibiotics and antiviral agents, analgesics, anorexics, anthelmintics, antiarthritics, antiasthma agents, anticovulsants, antidepressants, antidiabetic agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomiemetcs, sedatives and tranquilizers.

For topical applications the agents include antibiotics, fungistatic and fungicidal agents, corticosteroids, agents, antiemetics, antpruritic agents, vasodilators, bronchodilators, expectorants, analgesics, sunscreen compounds, collagen softening agents and other similar compounds. Cosmetic agents, hair and skin dyes, natural and synthetic hormones, perfumes, insect repellents, diagnostic agents and other such compounds may also be advantageously formulated with these penetration enhancers.

Some of these penetration enhancers can also be used by themselves as moisturizers in cosmetic formulations. Moreover, these penetration enhancers are useful in agriculture in the application of fertilizers, hormones, growth factors including micronutrients, insecticides, molluscicides, arachicides, nematocides, rodenticides, herbicides, and other pesticides to plants, animals and pests. These penetration enhancers are also useful for penetration of micronutrients in seeds for enhanced plant growth.

Of course, the appropriate dosage levels of all the physiologically active agents, without conjoint use of the penetration enhancing compounds of formula I, are known to those of ordinary skill in the art. These conventional dosage levels correspond to the upper range of dosage levels for compositions including a physiologically active agent and a compound of formula I as a penetration enhancer. However, because the delivery of the active agent is enhanced by compounds of the present invention, dosage levels significantly lower than conventional dosage levels may be used with success. Systemically active agents are used in amounts calculated to achieve and maintain theapeutic blood levels in a human or other animal over the period of time desired. (The term "animal" as used here encompasses humans as well as other animals, including particularly pets and other domestic animals.) These amounts vary with the potency of each systemically active substance, the amount required for the desired therapeutic or other effect, the rate of elimination or breakdown of the substance by the body once it has entered the bloodstream and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The present invention contemplates compositions of compounds of formula I, together with physiologically active agents from 0.05% to 100% of conventional dosage levels. The amount of carboxylic acid amide which may be used in the present invention is an effective, non-toxic amount for enhancing percutaneous abosrption. Generally, for topical use the amount ranges between 0.1 to about 10 and preferably about 0.1 to 5 percent by weight of the composition. For transdermal enhancement of systemic agents, the amount of pentration enhancer which may be used in the invention varies from about 1 to 100 percent although adequate enhancement of penetration is generally found to occur in the range of about 1 to 30 percent by weight of the formulation to be delivered. For transdermal use, the penetration enhancers disclosed herein may be used in combination with the active agent or may be used separately as a pre-treatment of the skin or other body membranes through which the active agent is intended to be delivered.

Dosage forms for application to the skin or other membranes of humans and animals include creams, lotions, gels, ointments, suppositories, sprays, aerosols, buccal and sublingual tablets and any one of a variety of transdermal device for use in the continuous administration of systemically active drugs by absorption through the skin, oral mucosa or other membranes, see for example, one or more of U.S. Pat. Nos. 3,598,122; 3,598,123; 3,731,683; 3,742,951; 3,814,097; 3,921,636; 3,972,995; 3,993,072; 3,993,073; 3,996,934; 4,031,894; 4,060,084; 4,069,307; 4,201,211; 4,230,105; 4,292,299 and 4,292,303. U.S. Pat. No. 4,077,407 and the foregoing patents also disclose a variety of specific systemically active agents which may also be useful as in transdermal delivery, which disclosures are hereby incorporated herein by this reference.

Typical inert carriers which may be included in the foregoing dosage forms include conventional formulating materials, such as, for example, water, ethyanol, 2-propanol (isopropyl alcohol), 1,2-propanediol (propylene glycol), 1,3-butanediol, 1,2,3-propanetriol (glycerol), propanone (acetone), butanone (methyl ethyl ketone), freons, polyvinyl pyrrolidone, frangrances, gel producing materials such as "Carbopol", stearyl alcohol, stearic acid, spermaceti, sorbitan monooleate, sorbital, "polysorbates", "Tweens", methyl cellulose etc.

The examples which follow illustrate the penetration enhancers and the compositions of the present invention.

EXAMPLE 1

Preparation of 1-hexanoylpyrrolidine

Hexanoyl chloride (13.46 g, 0.1M) was added gradually to a cooled, stirred solution of pyrrolidine (7,25 g, 0.1M) in 200 ml of benzene and dry pyridine (7.91 g, 0.1M). Two hours after the addition water was added. The organic layer was washed successively with 5% aqueous hydrochloric acid, saturated sodium bicarbonate solution, and saturated sodium chloride solution. The organic layer was dried over anhydrous sodium sulfate, filtered and concentrated. Distillation of the residue gave 13.52 g (80%) of a colorless oil, b.p. 98–100/7 mm.

The following compounds were prepared analogously by substituting equimolar amount of the corresponding carboxylic acid chlorides:

| | | |
|---|---|---|
| 1-octanoylpyrrolidine | 83% | 110–115/0.3 mm |
| 1-nonanoylpyrrolidine | 76% | 137/0.5 mm |
| 1-tetradecanoylpyrrolidine | 75% | 177–180/0.3 mm |
| 1-hexadecanoylpyrrolidine | 70% | 200–205/1 mm |

The following compounds are prepared analogously by substituting equimolar amounts of the corresponding carboxylic acid chlorides:
1-decanoylpyrrolidine
1-dodecanoylpyrrolidine

EXAMPLE 2

Preparation of 1-dodecanoylpiperidine

In a manner similar to that described in Example 1, dodecanoyl chloride (21.88 g, 0.1M) was treated with piperidine (8.52 g, 01M). Work up and distillation gave 16.55 g (62%) of the product, b.p. 185/2 mm.

The following compounds were prepared analogously by substituting equimolar amount of the corresponding carboxylic acid chlorides:

| | | |
|---|---|---|
| 1-pentanoylpiperidine | 70% | 122–125/10 mm |
| 1-hexanoylpiperidine | 71% | 101–102/0.5 mm |
| 1-heptanoylpiperdine | 70% | 158–162/12 m mm |
| 1-octanoylpiperidine | 69% | 101–102/0.3 mm |
| 1-nonanoylpiperidine | 67% | 105/0.1 mm |
| 1-decanoylpiperidine | | |
| 1-tetradecanoylpiperidine | 63% | 174/0.5 mm |
| 1-hexadecanoylpiperidine | 57% | 182/0.3 mm |

EXAMPLE 3

Preparation of 1-octanoylhexahydro-1H-azepine

In a manner similar to that described in Example 1, octanoyl chloride (16.26 g, 0.1M) was treated with hexahydro-1H-azepine (9.92 g, 0.1M). Work up and distillation of the residue gave 15.3 g (68%) of product, b.p. 122/0.8 mm.

The following compounds were prepared analogously by substituting equimolar amount of the corresponding carboylic acid chlorides:

| | | |
|---|---|---|
| 1-hexanoylhexahydro-1H—azepine | 66% | 112/0.8 mm |
| 1-nonanoylhexahydro-1H—azepine | 84% | 123–124/0.02 mm |
| 1-hexadecanoylhexahydro-1H—azepine | 63% | 205/0.5 mm |

EXAMPLE 4

Preparation of 1-dodecanoylhexahydro-1H-azepine

A mixture of dodecanoic acid (20.03 g, 0.1M), acetic anhydride (13.27 g, 0.13M), hexahydro-1H-azepine (12.9 g, 0.13M) was heated with distillation of formed acetic acid. The residue on distillation gave 23.46 g (83.5%) of colorless product, b.p. 204–205/7 mm.

The following compounds were prepared analogously by substituting equimolar amount of the corresponding carboxylic acids:

| | | |
|---|---|---|
| 1-butyrylhexahydro-1H—azepine | 63.2% | 133–4/11 mm |
| 1-pentanoylhexahydro-1H—azepine | 84% | 141–2/7 mm |
| 1-decanoylhexahydro-1H—azepine | 81% | 181–3/6 mm |

EXAMPLE 5

Preparation of 1-butyryl-2-carboxypyrrolidine(1-butyryl-L-proline)

11.4 m. (0.11m) of butyryl chloride and 20 ml of 7M NaOH (0.1M) were added in small portions into a chilled solution of L-proline (11.5 g, 0.1M) dissolved in 14.3 ml 7M NaOH (0.1M) according to the method of Kikuchi et. al., Biochim. Biophys. Acta 744,180 (1983). The reaction mixture was stirred vigorously during the addition and was always kept slightly alkaline. After the addition was over the reaction mixture was further stirred for an hour at 0–5 C. The mixture was then extracted with one portion of ethyl acetate and the aqueous layer was acidified with HCl to pH 1.8. The precipitated product was washed with cold water and dried in vacuo. recrystallization from acetone gave 14 g (82%) of the product.

The following compounds were similarly prepared by substituting equimolar amounts of the corresponding carboxylic acid chlorides:

1-hexanoyl-2-carboxypyrrolidine(1-hexanoyl-L-proline)
1-octanoyl-2-carboxypyrrolidine(1-octanoyl-L-proline)
1-decanoyl-2-carboxypyrrolidine(1-decanoyl-L-proline)
1-dodecanoyl-2-carboxypyrrolidine(1-dodecanoyl-L-proline)
1-tetradecanoyl-2-carboxypyrrolidine(1-tetradecanoyl-L-proline)
1-hexadecanoyl-2-carboxypyrrolidine(1-hexadecanoyl-L-proline)

EXAMPLE 6

The general procedure of Example 5 is repeated, except that the L-proline utilized therein is replaced, successively, with an equimolar amount of 2-piperidinecarboxylic acid and butyryl chloride is replaced, successively, with an equimolar amount of C6, C8, C10, C12, C–and C16 carboxylic acid chlorides to produce, respectively
1-hexanoyl-2-carboxypiperidine
1-octanoyl-2-carboxypiperidine
1-decanoyl-2-carboxpiperidine
1-dodecanoyl-2-carboxypiperidine
1-tetradecanoyl-2-carboxypiperidine
1-hexadecanoyl-2-carboxypiperidine

EXAMPLE 7

The general procedure of Example 5 is repeated, except that L-proline utilized therein is replaced, successively, with an equimolar amount of 3-piperidinecarboxylic acid and butyryl chloride is replaced, successively, with an equimoloar amount of C6, C8, C10, C12, C14 and C16 carboxylic acid chlorides to produce, respectively
1-hexanoyl-3-caroboxypiperidine
1-octanoyl-3-carboxypiperidine
1-decanoyl-3-carboxypiperidine
1-dodecanoyl-3-carboxypiperidine
1-tetradecanoyl-3-carboxypiperidine
1-hexadecanoyl-3-carboxypiperidine

EXAMPLE 8

The general procedure of Example 5 is repeated, except that L-proline utilized therein is replaced, successively, with an equimolar amount of 4-piperidinecarboxylic acid and butyryl chloride is replaced, successively, with an equimolar amount of C6, C8, C10, C12, C14 and C16 carboxylic acid chlorides to produce, respectively
1-hexanoyl-4-carboxypiperidine
1-octanoyl-4-carboxypiperidine
1-decanoyl-4-carboxypiperidine
1-dodecanoyl-4-carboxypiperidine
1-tetradecanoyl-4-carboxypiperidine
1-hexadecanoyl-4-carboxypiperidine

EXAMPLE 9

The following solution formulation is prepared

| | Solution % |
|---|---|
| Griseofulvin | 1 |
| 1-dodecanoylhexahydro-1H—azepine | 1 |
| Isopropyl myristate | 5 |
| Fragrance | 0.1 |
| Ethanol | 92.9 |

This formulation is effective in the treatment of fungus infections.

EXAMPLE 10

An aerosol form of the formulation of Example 10 is prepared by preparing the following mixture:

| | |
|---|---|
| Formulation | 25% |
| Freon[1] | 75% |

[1]Freon is 75/25 Freon 114/12

EXAMPLE 11

The following cream formulation is prepared:

| | % |
|---|---|
| Clindamycin base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 1-dodecanoylhexahydro-1H—azepine | 0.5 |
| Sorbitol solution, U.S.P. | 5.5 |
| Sodium citrate | 0.5 |
| Chemoderm #844 Fragrance | 0.2 |
| Purified water | 68.4 |

This formulation is effective in the treatment of acne.

EXAMPLE 12

The following solution formulations are prepared:

| | A (%) | B (%) |
|---|---|---|
| Clindamycin base | — | 1.0 |
| Clindamycin phosphate acid | 1.3 | — |

|  | A (%) | B (%) |
|---|---|---|
| Sodium hydroxide | 0.077 | — |
| 1 M Hydrochloric acid | — | 2.27 |
| Disodium edetate · 2H2O | 0.003 | 0.003 |
| Fragrances | 0.5 | 0.5 |
| 1-dodecanoylhexahydro-1H—azepine | 1.0 | 1.0 |
| Purified water | 20.0 | 17.73 |
| Isopropanol | 77.12 | 77.497 |

These solutions are effective for the treatment of acne in humans.

EXAMPLE 13

The following solution formulation is prepared:

|  | % |
|---|---|
| Neomycin sulfate | 0.5 |
| Lidocaine | 0.5 |
| Hydrocortisone | 0.25 |
| 1-dodecanoylhexahydro-1H—azepine | 0.5 |
| Propylene glycol | 98.25 |

This solution is effective for the treatment of otitis in domestic animals.

EXAMPLE 14

The following sunscreen emulsion is prepared:

|  | % |
|---|---|
| p-aminobenzoic acid | 2.0 |
| Benzyl alcohol | 0.5 |
| 1-dodecanoylhexahydro-1H—azepine | 1.0 |
| Polyethylene glycol 500-MS | 10.0 |
| Isopropyl lanolate | 3.0 |
| Lantrol | 1.0 |
| Acetylated lanolin | 0.5 |
| Isopropyl myristate | 5.0 |
| Light mineral oil | 8.0 |
| Cetyl alcohol | 1.0 |
| Veegum | 1.0 |
| Propylene glycol | 3.0 |
| Purified water | 64.0 |

EXAMPLE 15

The following antineoplastic solution is prepared:

|  | % |
|---|---|
| 5-fluorouracil | 5 |
| 1-dodecanoylhexahydro-1H—azepine | 0.1 |
| Polyethylene glycol | 5 |
| Purified water | 89.9 |

EXAMPLE 16

The following insect repellant atomizing spray is prepared:

|  | % |
|---|---|
| N,N—diethyltoluamide | 0.5 |
| 1-dodecanoylhexahydro-1H—azepine | 0.5 |
| Ethanol | 99 |

EXAMPLE 17

The following cream formulation may be prepared containing about 0.001 to 1 percent, with preferably 0.1 percent fluocinolone acetonide:

|  | % |
|---|---|
| Oil phase |  |
| Fluocinolone acetonide | 0.1 |
| 1-dodecanoylhexahydro-1H—azepine | 1 |
| cetyl alcohol | 9.5 |
| Stearyl alcohol | 1.5 |
| Glyceryl monostearate | 4 |
| Water phase |  |
| Propylene glycol | 10 |
| Sodium dodecyl sulfate | 0.1 |
| Deionized water q.s. | 100 |

The steroid is dissolved in the vehicle and added to a stirred, cooling melt of the other ingredients. The preparation is particularly useful for the treatment of inflamed dermatoses by topical application to the affected skin area. the amount of frequency of application of this steroid. Penetration of the steroid in the inflamed tissue is enhanced and a therapeutic level is achieved more rapidly and sustained for longer duration than when the steroid is applied in conventional formulation.

EXAMPLE 18

The following analgesic gel is prepared:

|  | % |
|---|---|
| Carbopol 934 | 1 |
| Indomethacin | 1 |
| Propylene glycol | 10 |
| Ethanol | 30 |
| Diisopropanolamine | 1.1 |
| Diisopropyl adipate | 2 |
| 1-dodecylhexahydro-1H—azepine | 2 |
| Water | 52.9 |

EXAMPLE 19

The following cream formulation is prepared:

|  | % |
|---|---|
| Isosorbide dinitrate | 10 |
| Glycerol monostearate | 5.5 |
| Polyoxyethylene stearate | 4.5 |
| C8-C18 fatty acid esters of a glycerol ethoxylated with about 7 moles of ethylene oxide | 8 |
| 1-dodecanoylhexahydro-1H—azepine | 2 |
| Sorbic acid | 0.165 |
| Ascorbyl palmitate | 0.055 |
| Citric acid | 0.1 |
| Na EDTA | 0.014 |
| Fragrance | 0.05 |
| Water | 69.616 |

This formulation is effective in the treatment of angina.

EXAMPLE 20

The following skin moisturizing formulation is prepared:

|  | % |
|---|---|
| Pyrrolidonecarboxylic acid Na | 1 |

| | % |
|---|---|
| Glycerine | 4 |
| Citric acid | 0.03 |
| Sodium citrate | 0.05 |
| Allantoin | 0.1 |
| Ethanol, 95% | 9 |
| Oleth-15 | 1 |
| Linoleic acid | 1 |
| 1-dodecanoyl-L—proline | 2 |
| Sunscreen agent | 0.1 |
| Water | 81.72 |

What is claimed is:

1. A composition useful for topically administering steroids through the skin and mucous membranes of humans and animals in a transdermal device or formulation for systemic use or to the skin of humans and animals for localized use comprising an effective amount of a physiologically active agent and a non-toxic, effective penetrating amount of a compound having the structural formula

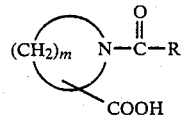

where R is an alkyl group with 1 to 19 carbon atoms, and m is 4, 5 or 6.

2. A composition comprising an effective amount of a steroid and an effective penetrating amount of a compound having the structural formula

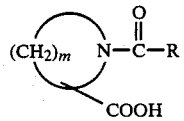

where R is an alkyl group with 1 to 19 carbon atoms, and m is 4, 5 or 6.

3. The composition of claim 1 wherein the physiologically active agent is physiologically active steroid.

* * * * *